United States Patent
Vaisnys et al.

(10) Patent No.: US 8,014,859 B2
(45) Date of Patent: Sep. 6, 2011

(54) EXTERNAL DEFIBRILLATOR ENCLOSURE WITH ACCESSORY STORAGE SLOT

(75) Inventors: Gintaras A. Vaisnys, Chicago, IL (US); Glenn W. Laub, Princeton, NJ (US); Giovanni C. Meier, Madison, CT (US); Benny S. Chi, Dumont, NJ (US); James Sener, Glastonbury, CT (US)

(73) Assignee: Defibtech, LLC, Guilford, CT (US)

( * ) Notice: Subject to any disclaimer, the term of this patent is extended or adjusted under 35 U.S.C. 154(b) by 488 days.

(21) Appl. No.: 10/678,733

(22) Filed: Oct. 2, 2003

(65) Prior Publication Data

US 2005/0075671 A1    Apr. 7, 2005

(51) Int. Cl.
*A61N 1/39* (2006.01)

(52) U.S. Cl. .............................. 607/5; 607/145

(58) Field of Classification Search ............... 607/142, 607/29, 5, 145, 148, 149; 601/41, 15
See application file for complete search history.

(56) References Cited

U.S. PATENT DOCUMENTS

| | | | |
|---|---|---|---|
| 4,590,943 A | | 5/1986 | Paull et al. |
| 4,610,254 A | * | 9/1986 | Morgan et al. ............... 607/6 |
| D372,977 S | | 8/1996 | Bishay |
| 5,607,454 A | | 3/1997 | Cameron et al. |
| 5,645,571 A | | 7/1997 | Olson et al. |
| 5,741,305 A | | 4/1998 | Vincent et al. |
| D394,903 S | | 6/1998 | Barkley et al. |
| 5,817,151 A | * | 10/1998 | Olson et al. ............... 607/142 |
| D402,758 S | | 12/1998 | Barkley et al. |
| 5,868,794 A | * | 2/1999 | Barkley et al. ............... 607/5 |
| 5,935,152 A | | 8/1999 | Merry et al. |
| 6,021,349 A | | 2/2000 | Arand et al. |
| 6,048,640 A | * | 4/2000 | Walters et al. ............... 429/136 |
| 6,108,578 A | | 8/2000 | Bardy et al. |
| 6,125,298 A | * | 9/2000 | Olson et al. ............... 607/5 |
| 6,154,673 A | | 11/2000 | Morgan et al. |
| 6,181,102 B1 | | 1/2001 | Andrews et al. |
| 6,266,562 B1 | | 7/2001 | Leyde |
| 6,289,243 B1 | | 9/2001 | Lin et al. |
| 6,334,070 B1 | | 12/2001 | Nova et al. |
| 2002/0082644 A1 | * | 6/2002 | Picardo et al. ............... 607/1 |
| 2003/0023274 A1 | * | 1/2003 | Chesley et al. ............... 607/5 |
| 2003/0028219 A1 | * | 2/2003 | Powers et al. ............... 607/5 |
| 2003/0088276 A1 | * | 5/2003 | Covey et al. ............... 607/5 |

OTHER PUBLICATIONS

Merriam-Webster Dictionary Online, www.websters.com, defined: slot.*

* cited by examiner

*Primary Examiner* — Niketa I Patel
*Assistant Examiner* — Alyssa M Alter
(74) *Attorney, Agent, or Firm* — King & Spalding LLP (57) ABSTRACT

An external defibrillator enclosure for use in conjunction with a defibrillator accessory, such as an electrode pad assembly, includes a front panel and a rear panel which are mated together and secured by a coupling means. The enclosure also includes a plate secured by a coupling means to the second panel. The plate and second panel are positioned relative to each other to form a slot that is sized to receive a portion of the electrode assembly. The enclosure also includes a connector port that allows for the electrode pad assembly to be pre-connected to the electronics within the enclosure. The electrode pad assembly includes a cable and a connector at the end of the cable, and the exterior face of enclosure rear panel includes a groove that is sized to receive and retain the cable. The groove holds the cable in place against the surface of the enclosure while the cable is connected to the connector port.

16 Claims, 8 Drawing Sheets

EXTERNAL DEFIBRILLATOR ENCLOSURE WITH ACCESSORY STORAGE SLOT

BACKGROUND OF THE INVENTION

1. Field of the Invention

The invention relates generally to external defibrillators and, more particularly, to an external defibrillator enclosure having a storage slot for storing defibrillator accessories such as an electrode pad assembly.

2. Description of Related Art

There are two traditional methods of storing accessories, such as electrode pads, for use with an external defibrillator. In one method a separate case is provided with the defibrillator. The case holds the defibrillator itself and other accessories, including electrode pads. In another method, the external defibrillator enclosure includes a storage compartment with an attached lid that opens and closes. Each of these configurations has its disadvantages.

For the separate-case configuration, the disadvantages include increased costs associated with manufacturing and buying the separate case and user inconvenience. Regarding user inconvenience, the separate case is essentially an extra part that the user must, not only pay for, but also carry around and periodically maintain. Furthermore, the case necessarily encloses the defibrillator thus requiring the user to open the case and remove the defibrillator and accessories in order to use the defibrillator.

For the lid configurations, one disadvantage relates to design and manufacturing complications associated with a lid. These complications relate to the location, orientation and operation of the lid and generally add to the cost of the device. Another disadvantage relates to the fact that often times a lid will break off. Once this occurs, the storage area for the electrode pads is essentially lost. In some external defibrillators, the opening of the lid automatically turns the device on. Thus, for these defibrillators, another disadvantage of the lid is that, if the lid does break off the device cannot be turned off. Yet another disadvantage of the lid configuration stems from the fact that the lid often covers the operational components of the defibrillator, such as the on/off button, shock button and operation indicators. Thus, in order to see and gain access to these components, the lid must be opened and the accessories removed.

Hence, those skilled in the art have recognized a need for providing an external defibrillator enclosure that provides for storage and access to accessories, e.g., electrode pads, battery packs, data cards, etc., in a manner that avoids the complications associated with known devices. The invention fulfills these needs and others.

SUMMARY OF THE INVENTION

Briefly, and in general terms, the invention is directed to an external defibrillator enclosure for use in conjunction with a defibrillator accessory, such as an electrode pad assembly. The enclosure includes one or more "built-in" slots that are sized to receive a portion of an accessory. While the term "slot" generally connotes a narrow opening, the term, as used herein is meant to encompass a compartment-like space of any dimension that is formed on or formed in the enclosure.

By providing a slot for an accessory, such as an electrode assembly, the external defibrillator enclosure allows for an all-in-one defibrillator system without the necessity of either a separate carrying case or a lid that opens and closes. Thus, the disadvantages associated with known external defibrillator configurations are avoided.

In one configuration, the enclosure includes a first or front panel and a second or rear panel which are mated together and secured by a coupling means. The enclosure also includes a plate secured by a coupling means to the second panel. The plate and second panel are positioned relative to each other to form a slot. In another configuration, the slot is formed in the second panel during the molding process, thus the separate plate is eliminated. In yet another configuration, the enclosure is formed as a single, unitary piece having identifiable portions, e.g., a front portion and a rear portion, one of which includes or carries the slot.

In one embodiment, the slot is sized to receive only a portion of a disposable electrode pad assembly. Because only a portion of the electrode pad assembly is received by the slot, a portion of the pad assembly is visible to the user. The electrode pad assembly packaging is configured to include information, such as the assembly's expiration date, in the visible area. Partial expose of the electrode assembly package also allows for quick and easy access to the electrode assembly during use. These features allowed by the slotted enclosure, provide an external defibrillator that is convenient and intuitive for people to use.

In a detailed configuration, the enclosure includes a connector port that allows for the electrode pad assembly to be pre-connected to the electronics within the enclosure. The electrode pad assembly includes a cable and a connector at the end of the cable, while the exterior face of the second or rear panel or rear portion of the enclosure includes a groove that is sized to receive and retain the cable. The groove holds the cable in place against the surface of the enclosure while the cable is connected to the connector port. Thus there are no dangling or loose cables associated with the external defibrillator when the device is not in use.

In another aspect, the invention relates to a disposable electrode pad assembly for storage in a portable automatic external defibrillator enclosure having a slot. The assembly includes a pair of electrode pads and a packaging having a profile configured to receive and enclose the pads. The profile of the packaging is further configured to facilitate insertion of a portion of the pads into the slot. In one configuration, this facilitation is provided by curving the corners of the packaging at the end intended to be inserted into the slot.

These and other aspects and advantages of the invention will become apparent from the following detailed description and the accompanying drawings which illustrate by way of example the features of the invention.

DETAILED DESCRIPTION OF THE PREFERRED EMBODIMENTS

Figure 1:
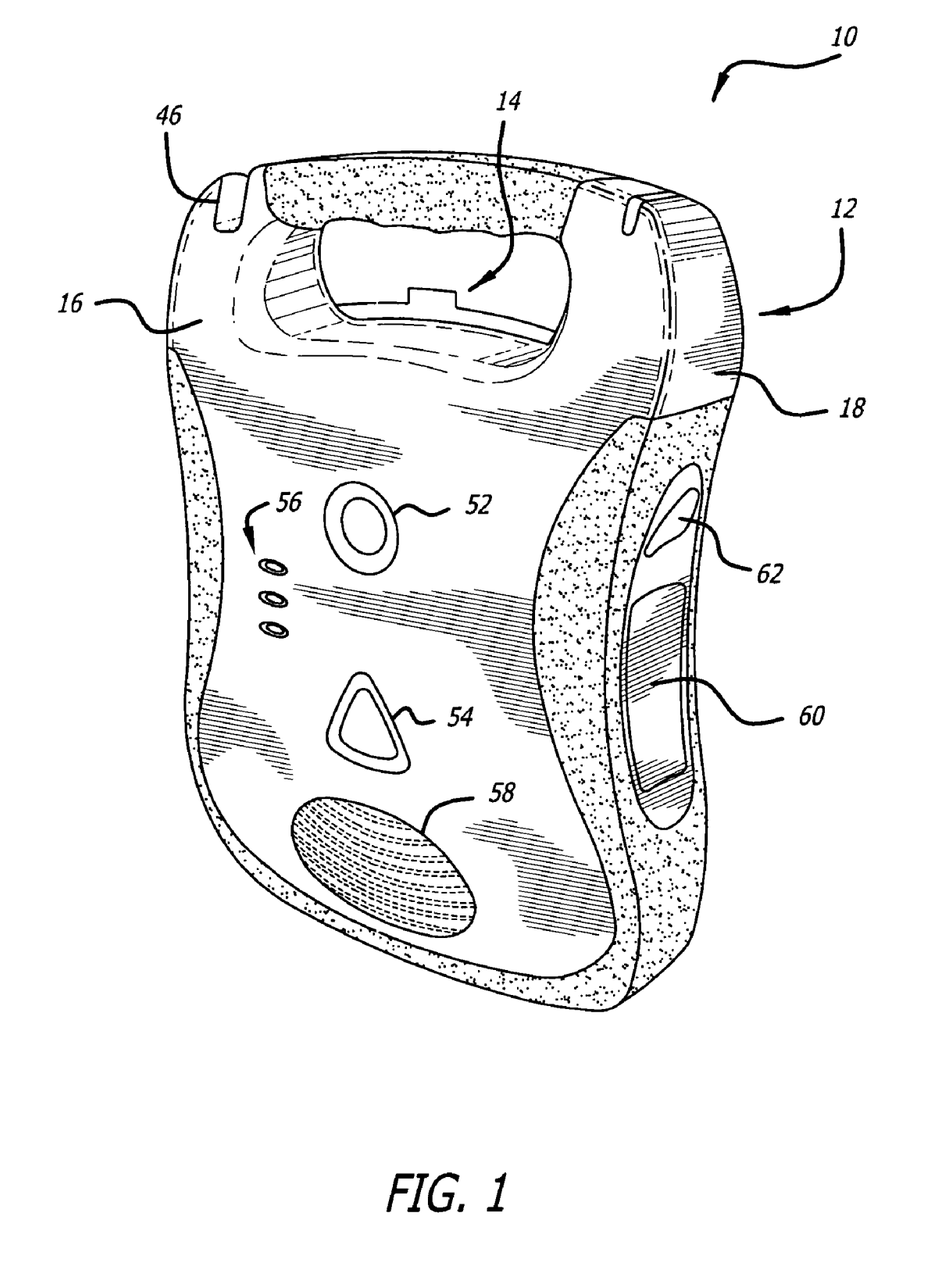
FIG. 1 is a perspective view of an external defibrillator including an enclosure having a slot (not visible) and electrode pad assembly.

Referring now to the drawings, wherein the reference numerals denote like or corresponding parts throughout the figures, and particularly to FIG. 1, there is shown a portable external defibrillator 10 configured in accordance with the invention. The defibrillator 10 includes an enclosure 12 and an electrode pad assembly 14 (only partially visible) that interfaces with the enclosure. Housed within the enclosure 12 is electrical means or circuitry that is configured to deliver a defibrillation pulse through the electrode pad assembly 14. Exemplary electrical circuits which may be used are disclosed in U.S. Pat. Nos. 5,607,454 and 5,645,571, the disclosures of which are hereby incorporated by reference. Alternate circuitry, within the purview of one of ordinary skill in the art, may be developed and employed. Thus, the scope of this invention is not intended to be limited to the circuitry described in the incorporated references.

Figure 2:
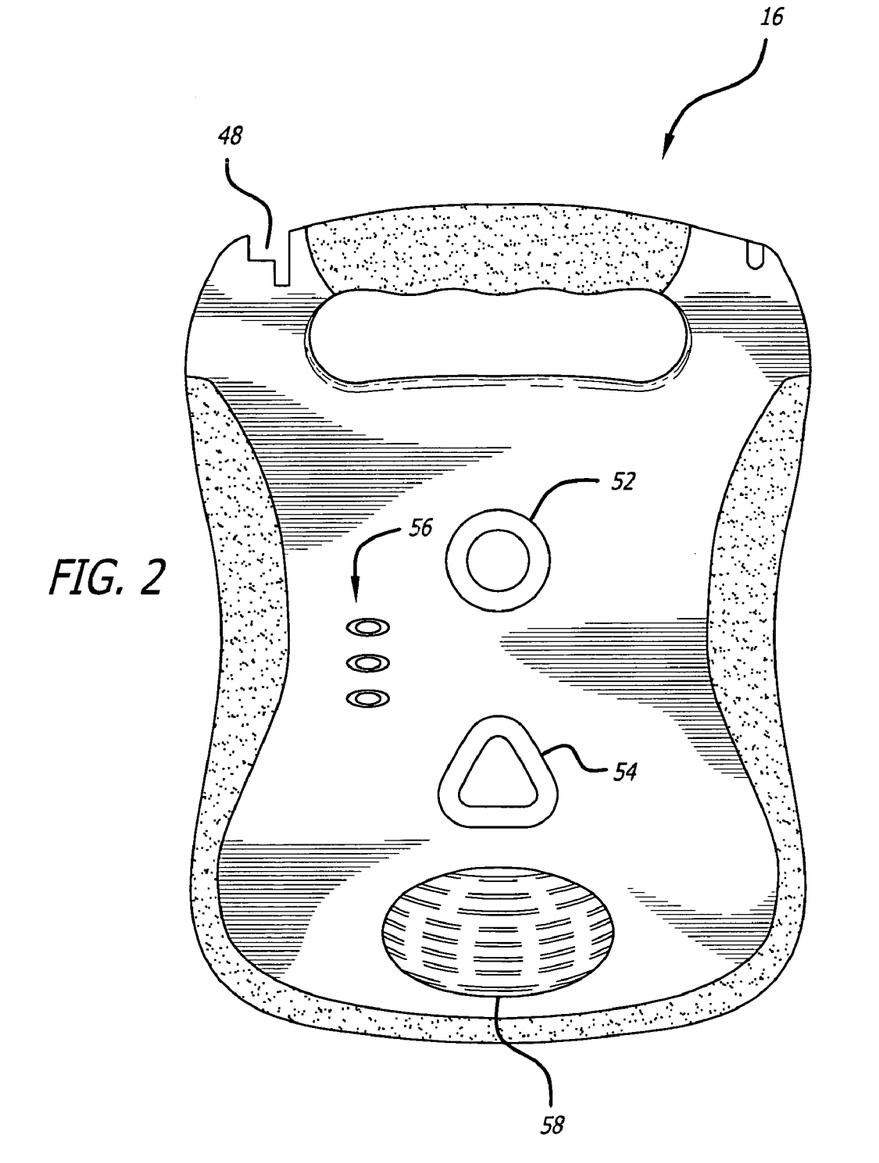
FIG. 2 is a plan view of a first, or front panel of the enclosure.
Figure 3:
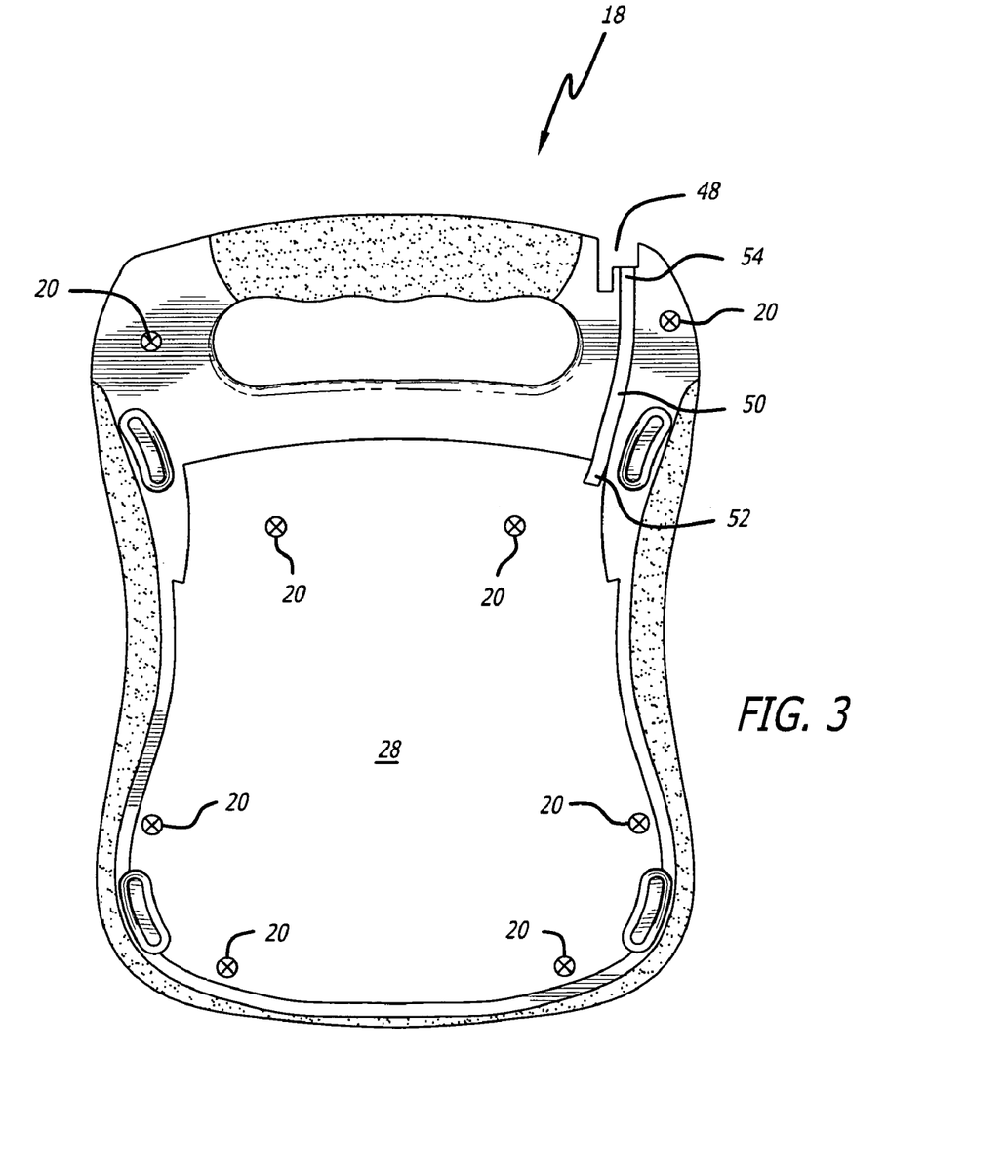
FIG. 3 is a plan view of a second, or rear panel of the enclosure.

With reference to FIGS. 1-3, the enclosure 12 includes a first panel or front panel 16 and a second panel or rear panel 18. In one embodiment, the panels 16, 18 are plastic molded parts. The two panels 16, 18 are mated together by a coupling means 20. The coupling means 20 may be screws, a snap fit engagement or any other structure or configuration capable of securing the panels 16, 18 together.

Figure 4:
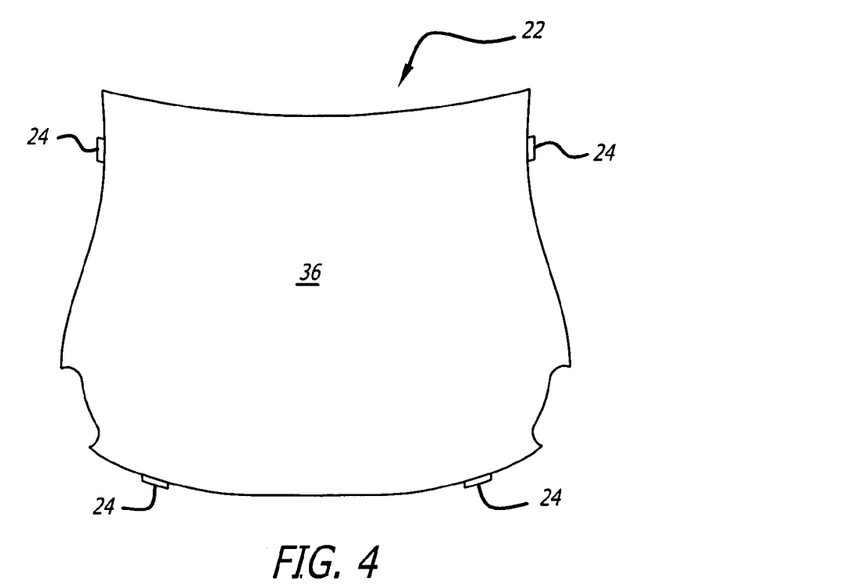
FIG. 4 is a plan view of the exterior side of a plate of the enclosure.
Figure 5:
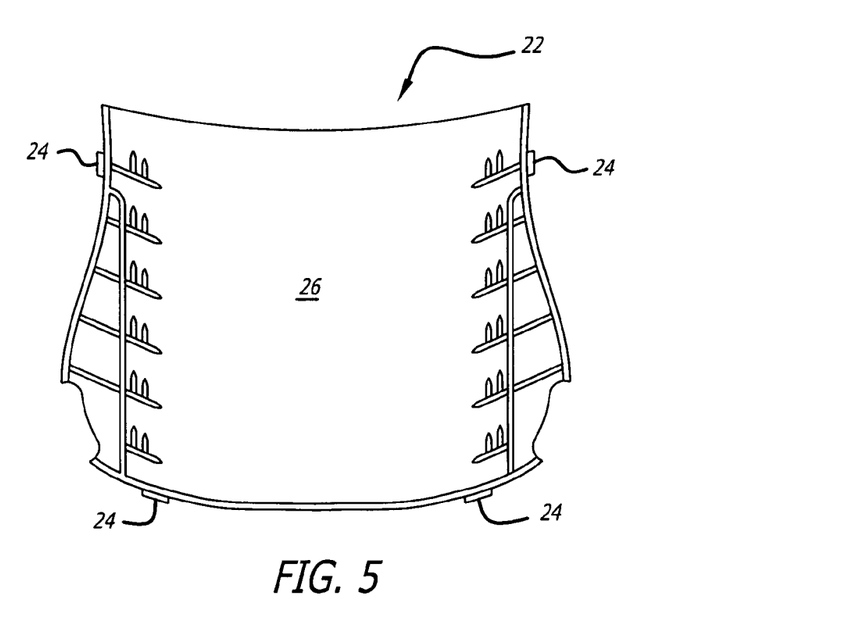
FIG. 5 is a plan view of the interior side of the plate.

With reference to FIGS. 4 and 5, the enclosure 12 also includes a plate 22 that is secured to the second panel 18 by a coupling means 24. In a one embodiment, this coupling means 24 is provided by a snap fit engagement between the plate 22 and the rear panel 18. In the preferred embodiment, the plate 22 is a continuous piece of material. In other configurations, the plate 22 may be discontinuous. For example, the plate 22 may have an opening or window in the center or some other section of the plate. Alternatively, the plate 22 may be generally U-shaped. Such configurations reduce the amount of plastic material required and allow exposure of more of the electrode pad assembly.

Figure 6:
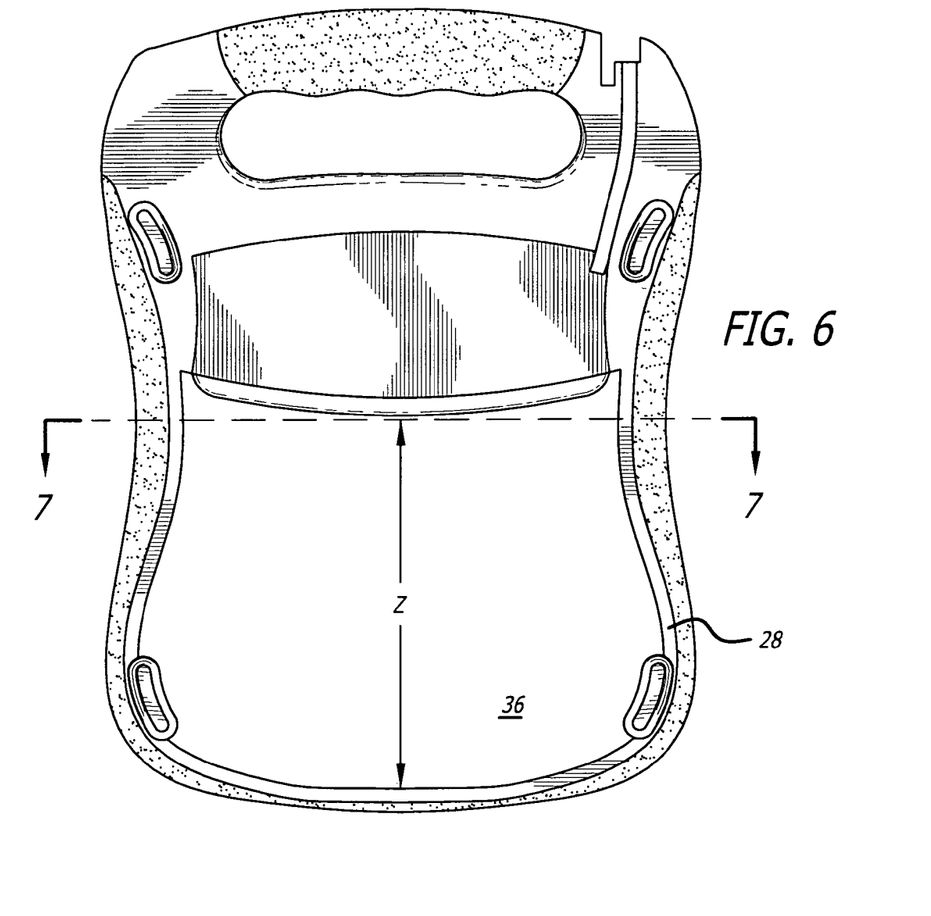
FIG. 6 is a plan view of the rear side of the enclosure with the plate of FIG. 4 attached to the rear panel.
Figure 7:
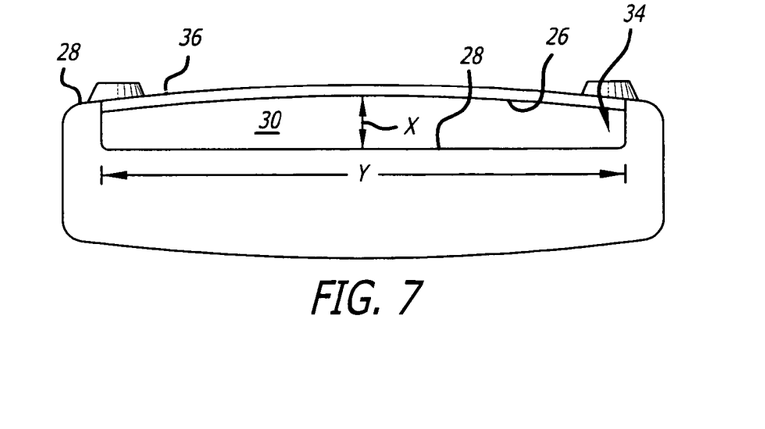
FIG. 7 is a cross section of the enclosure along line 7-7 of FIG. 6.

The plate 22 is positioned relative to, and engages the rear panel 18 such that its interior surface or side 26 (FIG. 5) faces the exterior surface or side 28 (FIG. 3) of the rear panel 18. With reference to FIGS. 6 and 7, the space between the interior surface 26 of the plate 22 and the exterior surface 28 of the rear panel defines a slot 30. The slot 30 is sized, height-wise x and width-wise y, to receive the electrode pad portion 32 (shown in FIG. 8) of the electrode pad assembly 14. The depth z (FIG. 6) of the slot 30 is sized to receive only a part of the electrode pad portion 32, thus leaving a part of the electrode pad portion exposed. The exposed portion of the electrode pad portion 32 allows for the visibility of critical pad information, such as the expiration date. The exposed portion also allows for easy access of the electrode pads during use. The height of the slot 30 may be varied by recessing the rear panel 18 in the area opposite the plate 22. The recess 34 in the rear panel 18 is formed during the molding of the rear panel.

The inclusion of the recess 34 allows for the exterior surface or side 36 of the plate 22 to be flush with the outer exterior surface 28 of the rear panel 18. This eliminates an abrupt transition between the plate 22 and the rear panel 18 and provides a more esthetically pleasing enclosure.

In the preferred embodiment, the slot 30 is formed between two separate parts, the rear panel 18 and the plate 22. In an alternate configuration, the rear panel may be formed, such as during the molding process, to include the slot 30, thus eliminating the need for the plate 22. In yet another configuration, the enclosure 12 may be formed as a single, unitary piece, having identifiable portions, such as a front portion and a rear portion, with the slot 30 formed in a portion of the unitary piece. Access to the interior of the enclosure may be obtained by providing a removable handle.

Figure 8:
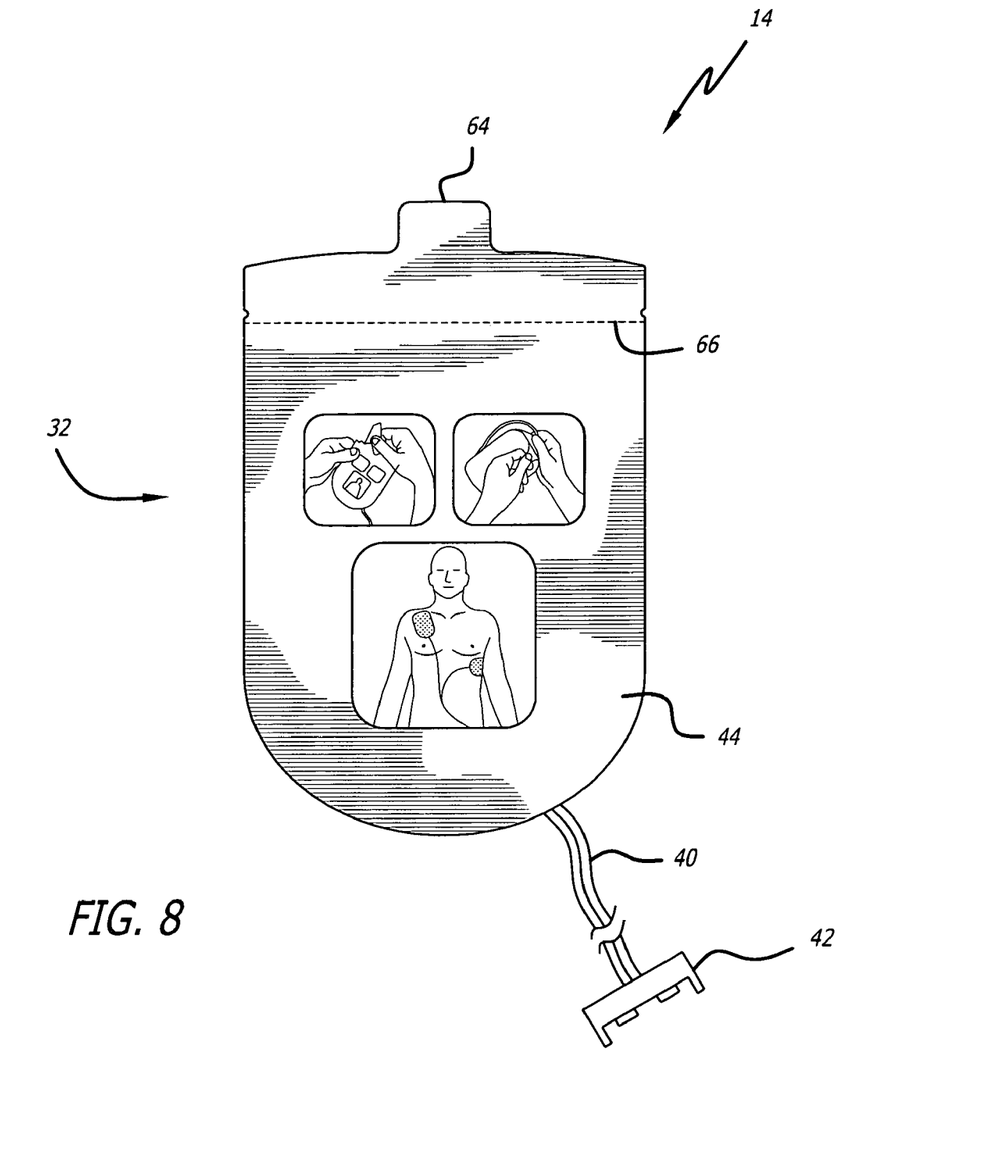
FIG. 8 depicts a disposable electrode pad assembly including a pair of electrode pads within a sealed package, and a cable and a connector exterior the sealed package.
Figure 9:
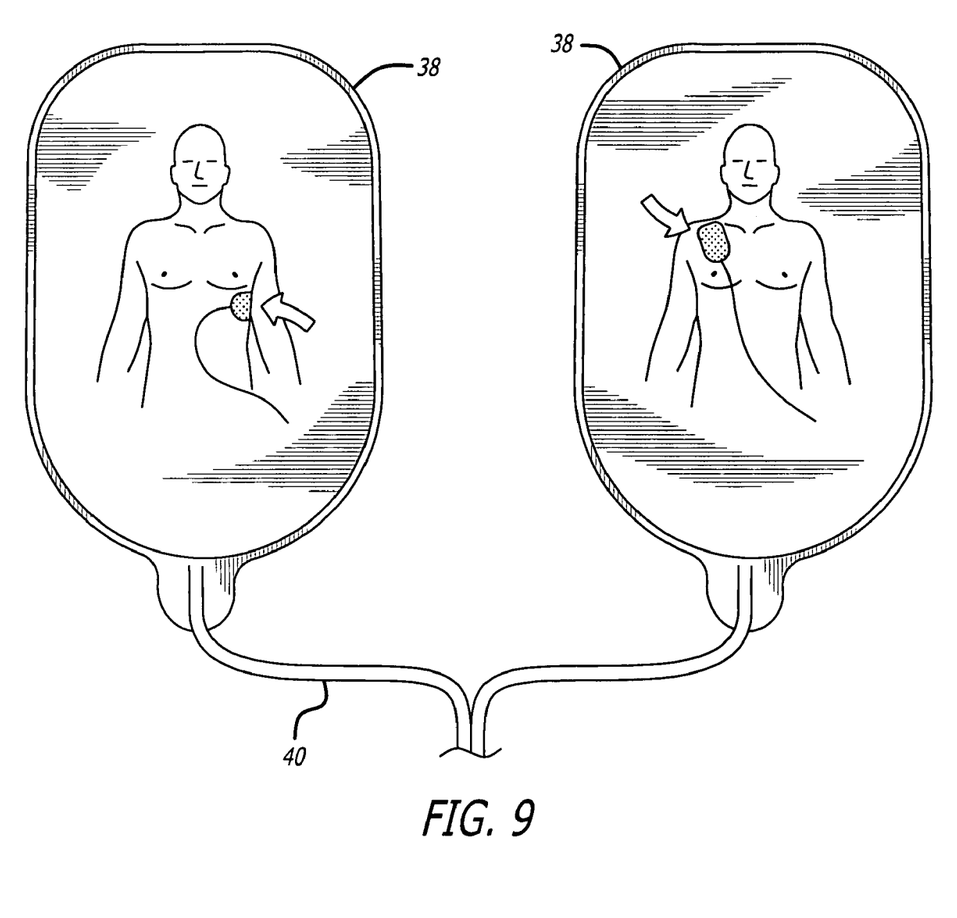
FIG. 9 depicts the electrode pads.

With reference to FIGS. 8 and 9, the electrode assembly 14 includes a pair of electrode pads 38, an electrical cable 40 and an electrical connector 42 connected to the end of the cable. The electrode pads 38 are housed within a sealed package 44. The electrode pads 38 and sealed package 44 form the previously referred to electrode pad portion 32 of the electrode assembly 14. A portion of the electrical cable 40 and the connector 42 are located outside of the sealed package 44. This allows for the electrode assembly 14 to be pre-connected to the electronics in the enclosure 12 and thus allows for rapid deployment during an emergency. The exterior surface of the housing of the electrical connector 42 includes a groove (not shown) that is sized to receive the electrical cable 40 to hold it in place, similar to the groove 50 (FIG. 3) in the rear panel 18.

The sealed package 44 including the electrode pads 38 has a shape or profile that facilitates easy insertion and removal of the electrode pad portion 32 from the slot 30. The shape essentially includes curved corners at the end intended to be inserted into the slot 30. The curved corners generally correspond to the shape of the corners in the electrode pads 38. Shaping the package as such essentially eliminates material that may otherwise interfere with the boundaries of the slot 30 during insertion of the package into the slot. A tab 64 is located at the other end of the package 44 and provides for easy gripping of the package during removal of the electrode pad assembly from the slot. The package 44 includes a perforation portion 66 that provides for easy opening of the package.

With reference to FIG. 1, the enclosure 12 includes a connector port 46 which provides for the electrical interface between the electrode pad assembly 14 at the exterior of the enclosure 12 and the defibrillation electronics inside the enclosure. The port 46 is provided by forming the front and rear panels 16, 18 to include a notch 48. When the panels 16, 18 are mated together during the defibrillator assembly process an electrical connector is positioned at the notches 48 to provide the connector port 46. The notches 48 are sized and configured such that the sides of the connector 42 are substantially flush with the adjacent surfaces of the front panel 16 and the rear panel 18.

With reference to FIG. 3, the exterior surface 28 of the rear panel 18 includes a means of holding the exposed portion of the electrical cable 40 (FIG. 8). In one embodiment the means of holding is provided by a groove 50 formed in the rear panel 18. The groove 50 includes a first end 52 that terminates at the recess 34 and a second end 54 that terminates at the notch 48. The groove 50 is sized to receive and retain the cable 40, such that the surface of the cable is substantially flush with the surface of the rear panel 18.

Figure 10:
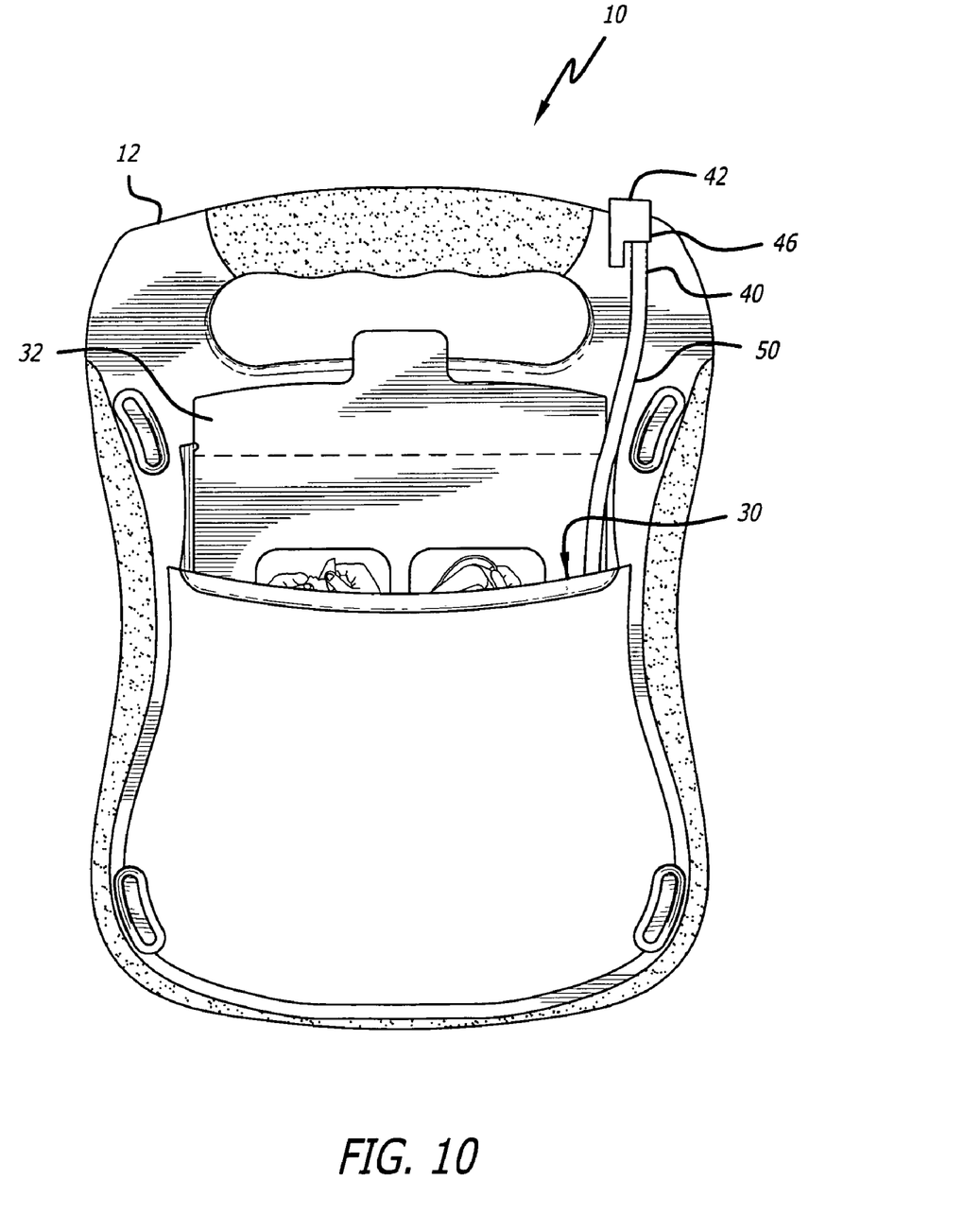
FIG. 10 is a rear plan view of an external defibrillator with an electrode pad assembly stored in the enclosure and electrically pre-connected to the enclosure.

With reference to FIG. 10, when the defibrillator 10 is not in use the electrode pad portion 32 of the electrode pad assembly 14 is positioned within the slot 30 such that a part of the electrode pad portion is exposed. The connector 42 is connected to the connector port 46 on the enclosure 12 and the exposed portion of the cable 40 is pressed into the groove 50.

During use of the defibrillator 10, the electrode pad portion 32 is pulled from the slot 30 and the exposed portion of the cable 40 is removed from the groove 50. The sealed package 44 is torn open and the electrode pads 38 are removed.

While the slot 30 provided in the enclosure 12 is described as functioning to hold the electrode pad portion 32 of the electrode pad assembly 14, the slot 30 may be configured to hold other defibrillator accessories, such as a spare battery pack or data card. The term "slot" is not intended to be limited to the specific configuration and dimensions shown in the embodiment described herein. A slot may have any shape necessary to perform its intended function, i.e., to receive and store a specific accessory. Alternatively, other slots may be added to the enclosure to provide storage for other accessories. For example, an enclosure may include both an electrode pad slot and a battery pack slot.

With reference to FIGS. 1 and 10, these slots or compartments in the enclosure are positioned away from other defibrillator components including the operational controls, i.e., the on/off button 52 and the shock button 54, indicator LEDS 56, speaker 58, battery pack 60 and battery pack removal button 62. Thus, the items stored in the slots are positioned to avoid interfering with the operation of the defibrillator.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An external defibrillator in combination with an electrode pad assembly, comprising:
a first panel and a second panel the first and second panels mated together and secured, the first and second panels containing defibrillator electronics therebetween;
a plate secured to the second panel, the plate and the second panel cooperating to define an enclosed volume accessed by a slot, the slot having a cross-section; and
an electrode pad assembly including an electrode pad portion containing electrode pads, the electrode pad portion having a cross-section that includes the electrode pads, the slot cross-section being greater than the electrode pad portion cross-section, at least a portion of the electrode pad positioned in the enclosed volume through the slot,
the electrode pad assembly further including an electrical cable with an electrical connector, the electrical cable extending from the electrode pads and out through the electrode pad portion to the electrical connector located outside the electrode pad portion, and
a connector port connected to the defibrillator electronics and located outside the enclosed volume, the connector port engageable with the electrical connector.

2. The combination of claim 1 wherein the slot is always present.

3. The combination of claim 1 wherein the electrical cable has a length sufficient to permit the electrical connector to engage the connector port.

4. The combination of claim 1 further including a connector port connected to the defibrillator electronics and located outside the enclosed volume, wherein the electrical cable has a length sufficient to permit the electrical connector to engage the connector port.

5. An external defibrillator in combination with an electrode pad assembly, comprising:
a first panel and a second panel, the first and second panels mated together and secured, the first and second panels containing defibrillator electronics therebetween;
a plate secured to the second panel, the plate and the second panel cooperating to define an enclosed volume accessed by a slot; and
an electrode pad assembly including an electrode pad portion containing electrode pads, at least a portion of the electrode pads positioned in the enclosed volume through the slot and removable from the enclosed volume through the slot,
the electrode pad assembly further including an electrical cable with an electrical connector, the electrical cable extending from the electrode pads and out through the electrode pad portion to the electrical connector located outside the electrode pad portion,
wherein the first panel has an exterior surface and the second panel has an exterior surface and one of the exterior surfaces comprises a temporary holding device for releasably securing the electrical cable to that exterior surface, the holding device being outside of the enclosed volume, and the electrical cable positioned therein.

6. The combination of claim 5 wherein the holding device comprises a groove formed in the exterior surface, the groove sized to receive and retain the electrical cable.

7. In combination, an electrode pad assembly and an external defibrillator, comprising:
an enclosure confining defibrillator electronics and defining an enclosed volume accessed by a slot;
a connector port connected to the defibrillator electronics and located outside the enclosed volume; and
an electrode pad assembly including an electrode pad portion containing electrode pads, at least a portion of the electrode pads positioned in the enclosed volume through the slot and removable from the enclosed volume through the slot, the electrode pad assembly further having an electrical cable with an electrical connector, the electrical cable extending from the electrode pads and out through the electrode pad portion to the electrical connector, the electrical connector located outside the electrode pad portion and connected to the connector port.

8. The combination of claim 7 wherein the slot is always present.

9. The combination of claim 8 wherein the enclosure has an exterior surface and the exterior surface comprises a groove sized to receive and retain the electrical cable.

10. The combination of claim 7 wherein the enclosure defines a handle and the connector port is adjacent the handle.

11. The combination of claim 7 further including a battery pack wherein the battery pack is positioned in the slot.

12. The combination of claim 7, wherein the electrode pad portion is removable from the volume through the slot in a direction of the connector port.

13. An external defibrillator in combination with an electrode pad assembly, comprising:
an enclosure confining defibrillator electronics and defining an enclosed volume accessed by a slot;
a connector port connected to the defibrillator electronics and located outside the enclosed volume; and
an electrode pad assembly including an electrode pad portion containing electrode pads, at least a portion of the electrode pads positioned in the enclosed volume through the slot and removable from the enclosed volume through the slot, the electrode pad assembly further having an electrical cable extending from the electrode pads and out through the electrode pad portion to an electrical connector, wherein the enclosure has an exterior surface, a holding device for releasably securing the electrical cable being on the exterior surface and the electrical cable is positioned in the holding device.

14. The combination of claim 13 wherein the holding device comprises a groove sized to receive and retain the electrical cable.

15. An external defibrillator, comprising:

an enclosure confining defibrillator electronics and defining an enclosed volume accessed by a slot, the enclosed volume adapted to hold at least a portion of an electrode pad portion containing electrode pads, the electrode pad portion being part of an electrode pad assembly, at least a portion of the electrode pad being positionable in the enclosed volume through the slot and removable from the enclosed volume through the slot, the electrode pad assembly further including an electrical cable and an electrical connector, the electrical cable extending from the electrode pads and out through the electrode pad portion to the electrical connector, the electrical connector located outside the electrode pad portion and being connectable, while at least part of the electrode pad assembly is positioned in the enclosed volume, to a connector port located outside the enclosed volume and connected to the defibrillator electronics wherein the enclosed volume is oriented relative to the connector port such that when the electrode pad portion is removed from the enclosed volume through the slot, a direction of movement of the electrode pad is toward the connector port.

16. The external defibrillator of claim 15, wherein the enclosure has an exterior surface, a holding device for securing the electrical cable being on the exterior surface.

* * * * *